United States Patent [19]  [11] 3,976,768
Nara et al.  [45] Aug. 24, 1976

[54] FORTIMICIN A

[75] Inventors: Takashi Nara, Tokyo; Seigo Takasawa, Hadano; Ryo Okachi, Machida; Isao Kawamoto, Machida; Mitsuyoshi Yamamoto, Machida; Seiji Sato, Machida; Tomoyasu Sato, Machida, all of Japan

[73] Assignee: Abbott Laboratories, North Chicago, Ill.

[22] Filed: July 22, 1974

[21] Appl. No.: 490,668

[30] Foreign Application Priority Data
July 23, 1973  Japan.............................. 48-80866

[52] U.S. Cl. ................................................ 424/118
[51] Int. Cl.² ........................................ A61K 35/00
[58] Field of Search...................... 424/118; 195/81

[56] References Cited
OTHER PUBLICATIONS

Miller, The Pfizer Handbook of Microbial Metabolites, McGraw-Hill Book Co., Inc., N.Y., N.Y., 1961 pp. 595 & 596.

Primary Examiner—Jerome D. Goldberg
Attorney, Agent, or Firm—Fitzpatrick, Cella, Harper & Scinto

[57] ABSTRACT

A new antibiotic, Fortimicin A, is produced by fermentation of a microorganism belonging to the genus Micromonospora. The antibiotic is accumulated in the culture medium and is isolated therefrom.

1 Claim, 2 Drawing Figures

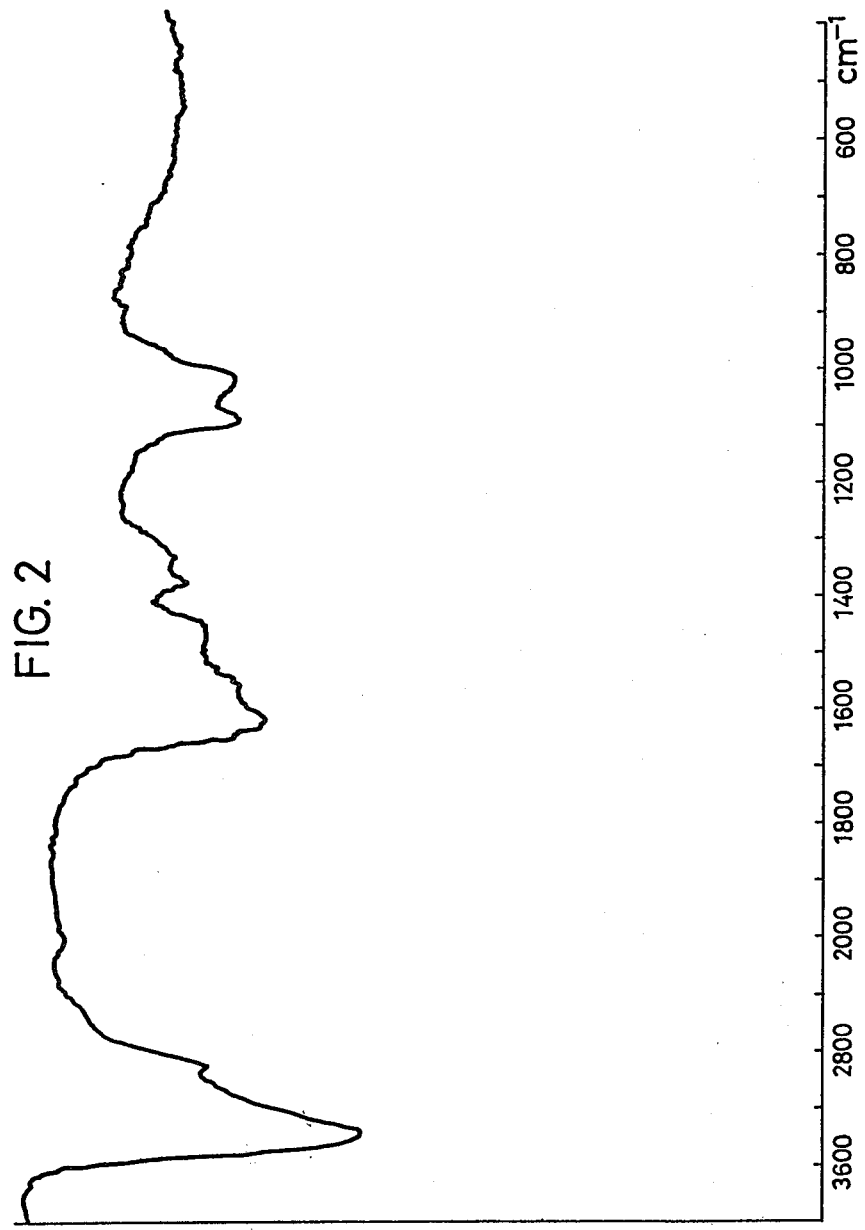

FORTIMICIN A

RELATED APPLICATIONS

The present invention is related generally to the invention disclosed in application Ser. No. 458,422, filed Apr. 5, 1974 and entitled "Fortimicin B and Process for Production Thereof".

BACKGROUND OF THE INVENTION

The present invention relates to a new antibiotic Fortimicin A, and a process for the production thereof. More specifically, the present invention pertains to the production of Fortimicin A by culturing a microorganism belonging to the genus Micromonospora until antibacterial activity is exhibited in the culture liquor and then isolating Fortimicin A therefrom.

Antibiotics which exhibit activity against a broad spectrum of bacteria are always in demand. To this end, a new species of microorganism has been isolated from the soil of a paddy field located in the suburbs of Hiroshima city in Hiroshima prefecture, Japan. This new species, when cultured, produces the new antibiotic, Fortimicin A, which exhibits an antibacterial activity against various Gram-positive and Gram-negative bacteria. Accordingly, the new antibiotic may be utilized for various purposes and is particularly useful as a surface disinfectant for controlling the population of Staphylococci, Escherichia and other bacteria.

BRIEF DESCRIPTION OF THE DRAWINGS

FIG. 2 illustrates the infra-red absorption spectrum of Fortimicin A.

SUMMARY OF THE INVENTION

Figure 1:
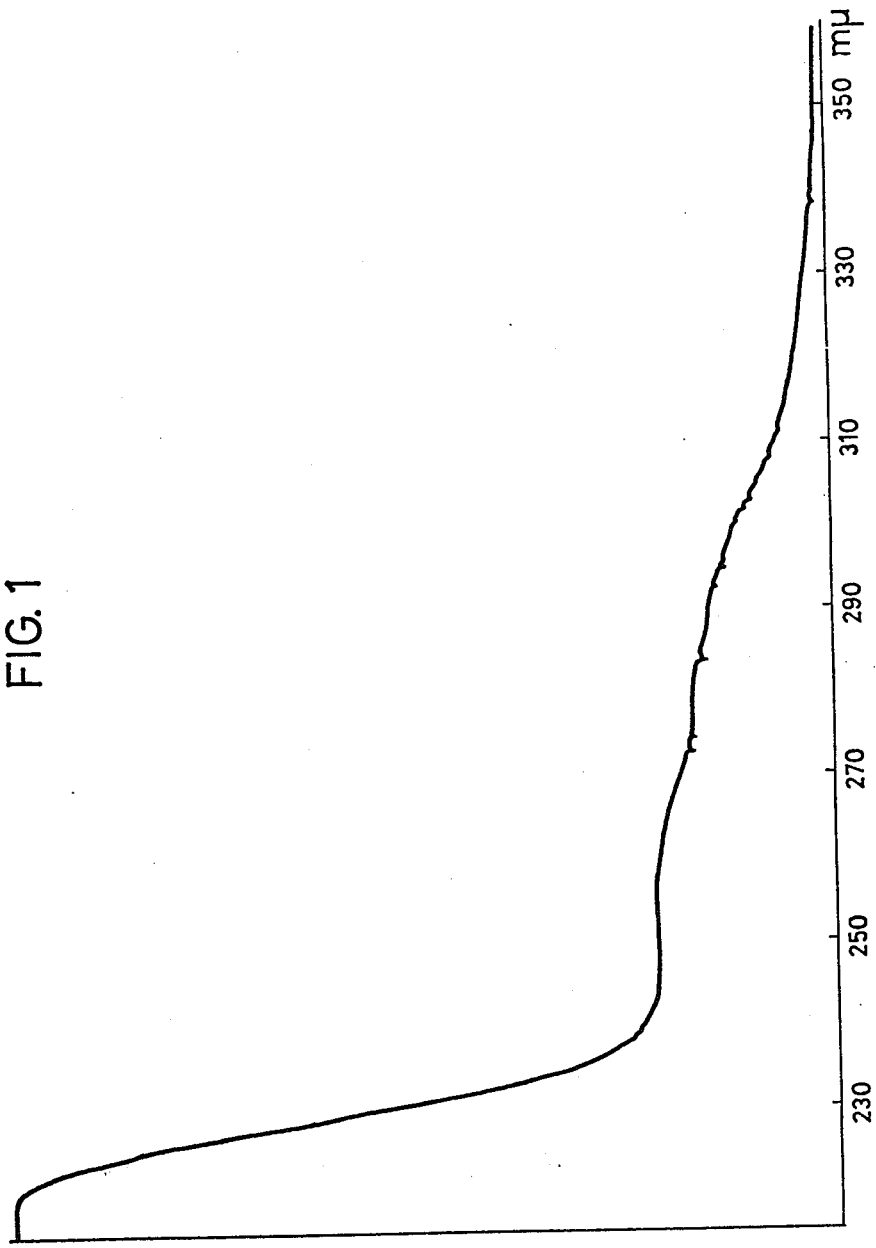
FIG. 1 illustrates the ultraviolet absorption spectrum of Fortimicin A.

In accordance with the present invention, a new antibiotic, Fortimicin A, is produced by fermentation of a microorganism belonging to the genus Micromonospora, which is capable of producing the antibiotic, in a nutrient medium until substantial antibacterial activity is detected in the culture liquor. At the completion of culturing, the antibiotic is isolated from the culture liquor by known means such as by ion exchange resin treatment.

DESCRIPTION OF THE INVENTION

The new antibiotic of the present invention was initially identified as XK-70-1, and has now been named Fortimicin A. It is believed to have the following chemical structure:

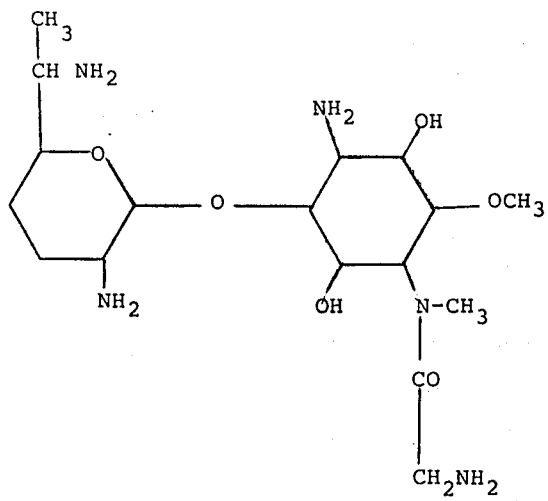

Fortimicin A is produced by fermentation of a microorganism belonging to the genus Micromonospora. A particularly suitable microorganism belongs to *Micromonospora olivoasterospora* which is determined to be a heretofore unidentified new species. Its typical strain was originally identified as strain MK-70. This strain has been deposited with the American Type Culture Collection, Rockville, Maryland and has been accorded accession number ATCC 21819. The MK-70 strain has the following properties:

I. Morphology

The MK-70 strain is Gram-positive. On conventional agar medium the MK-70 strain never forms a true aerial mycelium as observed with Streptomyces, etc. On the surface of an agar medium where there is a good spore formation there is observed an olive green, waxlike and lustrous layer of spores. When the strain is cultured in a liquid medium, the culture broth shows a light wheat color in the earlier stages of culturing, but in the later stages of culturing the culture broth shows a dark olive green color and a large number of spores are observed in the culture. By microscopic observation of the cells of the MK-70 strain cultured in a liquid medium, it has been found that the mycelium is about 0.5 $\mu$ in diameter and is well developed and non-septate. A single spore is formed at the end of each sporophore (about 0.3–1.0 $\mu$ in length) branched from the substrate mycelium, and the spores are formed along the relatively long substrate mycelia. The mature spores are spherical and about 1.0 $\mu$ in diameter. In observing the surfaces of the spores by an electron microscope, the spores look like a star since there are a large number of projections, whose tip ends are somewhat round.

II. Culture Characteristics

The degree of growth, surface state of colony and production of soluble pigments observed when the MK-70 strain is cultured on various media, are shown in Table 1. The color indications are given according to the classifications in the Color Harmony Manual (Container Corporation of America). Regarding the tyrosine medium, the medium described in Gordon & Smith: J. Bact. 69, 147 (1955) is used.

TABLE 1

| Medium | Growth | Color | Soluble pigment |
|---|---|---|---|
| Czapek's agar | Moderate Flat | Dusty olive (1 lg) | None |
| Glucose-asparagine agar | Moderate Flat, waxy | Olive (1 pl) | None |
| Nutrient agar | Good Raised ridged | Olive (1 pl) | None |
| Egg albumin agar | Moderate Flat, waxy | Light olive drab (1 li) | None |
| Starch agar | Good Flat | Black olive teak (1 po) | None |
| Malt extract-yeast extract agar | Good Raised, ridged | Dark olive (1 pn) | Dark olive (1½ pn) |
| Oatmeal agar | Good Plicate, waxy | Amber butterscotch (3 lc) dark brown (2 pn) | Dusty olive (1 pg) |
| Dextrose (1%) - NZ amine (3%) agar | Moderate Flat, waxy | Light wheat (2 ea) | None |
| Bennet's agar | Good Raised, ridged | Dark olive (1 pn) | None |

TABLE 1-continued

| Medium | Growth | Color | Soluble pigment |
|---|---|---|---|
| Emerson's agar | Moderate Raised, ridged, waxy | Olive (1 ni) | None |
| Glucose-yeast extract agar | Good Raised, ridged waxy | Dark olive (1 pn) | None |
| Peptone-iron agar | Moderate Flat, waxy | Dark olive (1 nl) | None |
| Tyrosine agar | Moderate Flat, waxy | Olive (1 ni) | None |

III. Physiological Properties

Physiological properties of the MK-70 strain are shown in Table 2. In the tests except those on the optimum temperature and actions upon milk and cellulose, the strain is cultured at 27°C for 2 weeks. The optimum temperature is determined after 5 days of culturing and the actions upon milk and cellulose are observed after one month of culturing.

TABLE 2

| (1) | Utilization of carbon sources: Carbon Sources: | Utilization: |
|---|---|---|
| | D-Arabinose | − |
| | D-Galactose | − |
| | D-Glucose | ++ |
| | Glycerol | − |
| | D-Lactose | − |
| | D-Fructose | − |
| | L-Inositol | − |
| | D-Mannitol | − |
| | D-Raffinose | − |
| | L-Rhamnose | − |
| | Sucrose | ++ |
| | Starch | ++ |
| | D-Xylose | − |
| (2) | Liquefaction of gelatin | Slightly positive |
| (3) | Action upon milk | Peptonized |
| (4) | Decomposition of cellulose | Slightly positive |
| (5) | Hydrolysis of starch | Positive |
| (6) | Optimum pH for growth | 6.8 − 7.5 |
| (7) | Optimum temperature for growth | 30°C − 38°C |
| (8) | Reduction of nitrate | Positive |
| (9) | Formation of tyrosinase | Negative |
| (10) | Formation of melanoid pigments | Negative |

The MK-70 strain is a mesophile, which never forms a true aerial mycelium when cultured on an agar medium, but forms single spores on the substrate mycelium, and it has been found by analysis that the cell wall of this strain contains meso-diaminopimelic acid. Accordingly, the MK-70 strain is regarded as a strain of the genus Micromonospora.

Reliable basis for the systematic classification of species of the genus Micromonospora have not been established. Therefore, the classification of the microorganisms of this genus has so far been conducted by an overall comparison of morphological and physiological properties, etc. There have been reported three strains belonging to the genus Micromonospora, that is, *Micromonospora echinospora* subsp. *echinospora* NRRL-2985 (ATCC 15837), *Micromonospora echinospora* subsp. *pallida* NRRL-2996 (ATCC 15838) and *Micromonospora echinospora* subsp. *Ferruginea* NRRL-2995 (ATCC 15836) which exhibit blunt spines on the surface of the spore. However, these three strains of *M. echinospora* form spores of dark brown to black color when cultured on a conventional agar medium, and never show an olive color as does the MK-70 strain.

The three strains of *M. echinospora* can utilize L-rhamnose, but the MK-70 strain cannot. Additionally, the three strains can produce two active substances, one of which has an activity only against Gram-positive bacteria and an Rf value of 0.4 to 0.5 in paper chromatography using water-saturated n-butanol as a developer, and the antibiotic Gentamicin having an Rf value of 0.00. On the other hand, the MK-70 strain can produce four distinct active substances, that is, a substance having an activity only against Gram-positive bacteria and having an Rf value of 0.05 to 0.1 in paper chromatography using the aforementioned developer; a substance having an activity only against Gram-positive bacteria and having an Rf value of 0.00; Fortimicin B, having an activity against Gram-positive and Gram-negative bacteria and having an Rf value of 0.00; and Fortimicin A which also is active upon Gram-positive and Gram-negative bacteria as well as having an Rf value of 0.00. As is evident from the above, the MK-70 strain is different from the three strains of *M. echinospora*.

The MK-70 strain shows an olive to dark olive color when cultured using a medium suitable for spore formation, and produces a soluble, olive pigment in some media. Among the strains of the genus Micromonospora, there are some strains capable of forming olive spores, i.e., *Micromonospora chalcea*, *Micromonospora fusca*, etc., but these are distinguished in the surface state of spores and the color of soluble pigments, etc.

Another species of Micromonospora, i.e., *Micromonospora coerulea* usually exhibits a green-blue color, and produces blue-green soluble pigments. The pigments function as an acid-base indicator and are, therefore, different from the pigment of the MK-70 strain. Moreover, the spores of *M. coerulea* are liable to disperse in a cluster state and the spore surfaces are smooth. Thus, *M. coerulea* is distinguished from the MK-70 strain.

As described above, there are no strains which correspond to the MK-70 strain among the strains of the genus Micromonospora so far reported. Therefore, the MK-70 strain is considered a new strain belonging to the genus Micromonospora and has been named *Micromonospora olivoasterospora*. The name of this species comes from the formation of olive spherical spores with projections.

As stated above, the MK-70 strain has been deposited with the American Type Culture Collection as Micromonospora sp. MK-70. The MK-70 strain has also been deposited with the Fermentation Research Institute, Tokyo, Japan, and has been assigned registration number FERMP-No. 1560.

Two variant strains of *Micromonospora olivoasterospora* have also been isolated which have the ability to produce Fortimicin A. These variants differ from the type strain in that they have the ability to utilize D-galactose, D-fructose and D-xylose. One variant additionally exhibits a light wheat color when cultured on various media since it lacks the ability to form spores on the mycelium. In other respects the variants closely resemble the type strain. These two variants have also been deposited with the American Type Culture Collection and have been assigned accession numbers ATCC 31009 and ATCC 31010. These variants, as well as the type strain are freely available to the public.

As is the case with other strains of Actinomycetes, the microorganisms useful in carrying out the present invention can undergo mutation by artifical means such as ultraviolet irradiation, $CO^{60}$ irradiation, X-ray irradiation and various mutation-inducing chemicals. Accordingly, any strain, even if thus mutated, is appropriate for the present invention insofar as it has the ability to produce Fortimicin A.

Generally, conventional methods for culturing microorganisms of the Actinomycetes may be employed in the process of the present invention. Thus, various nutrient sources may be employed for the culture medium. Appropriate carbon sources include glucose, starch, mannose, fructose, sucrose, molasses, etc., either alone or in combination. Additionally, hydrocarbons, alcohols, organic acids, etc., may be used depending upon the ability of utilization possessed by the particular microorganism. Inorganic and organic nitrogen sources such as ammonium chloride, ammonium sulfate, urea, ammonium nitrate, sodium nitrate, etc., and natural nitrogen sources such as peptone, meat extract, yeast extract, dry yeast, corn steep liquor, soybean meal, casamino acid, soluble vegetable protein, etc., may be used alone or in combination. In addition, such inorganic salts as sodium chloride, potassium chloride, calcium carbonate, potassium phosphates, etc., may be added to the medium, if necessary. Furthermore, organic or inorganic materials capable of promoting growth of the microorganism and the production of Fortimicin A may be properly added to the medium. Generally, we have found that when the production of Fortimicin A is enhanced by alteration of the culture medium constituents, the simultaneous production of other active substances decreases.

A liquid culturing method, especially a submerged stirring culturing method, is most suitable for the present process. It is desirable to carry out culturing at a temperature of 25° to 40°C and at an approximately neutral pH. The antibiotic of the present invention is formed and accumulated in the culture liquor usually after 4 to 15 days of culturing. When the yield of Fortimicin A in the culture liquor reaches a maximum, culturing is discontinued and the antibiotic is isolated and purified from the culture liquor obtained after the microbial cells have been removed such as by filtration.

Isolation and purification of Fortimicin A from the filtrate is carried out according to the methods usually used in the isolation and purification of microbial metabolic products from culture liquor.

Since Fortimicin A is basic and is soluble in water, but poorly soluble in the ordinary organic solvents, the antibiotic can be purified by the methods usually used for the purification of so-called water-soluble basic antibiotics. More specifically, Fortimicin A may be purified by a proper combination of adsorption and desorption from cation exchange resins; column chromatography using cellulose; Sephadex LH-20 (trade name, produced by Pharmacia Fine Chemicals Inc., U.S.A.); silica gel chromatography and the like methods.

For example, the cell-free culture filtrate is first adjusted to a pH of 7.5, and then subjected to adsorption on a cation exchange resin such as Amberlite (trade name, produced by Rohm & Haas Co., U.S.A.) IRC-50 ($NH_4^+$ form). After washing with water, elution is carried out with 1N aqueous ammonia. The active fraction is concentrated under reduced pressure and then passed through a column of anion exchange resin, such as Dowex (trade name, produced by Dow Chemical Co., U.S.A.) 1x2 ($OH^-$ form). The adsorbed substances are eluted with water, and the eluted active fractions are collected and concentrated under reduced pressure, whereby a crude powder containing Fortimicin A and other active components is obtained. The crude powder is then dissolved in water. The pH of the aqueous solution is adjusted to 5.0 with 2N sulfuric acid and then passed through a column of activated carbon. The active substances are thus adsorbed on the carbon. After washing the column with water to remove impurities, elution is carried out with 0.2N sulfuric acid. The eluted active fractions are collected and passed through a column of an anion exchange resin such as Dowex 44 ($OH^-$ form) for neutralization. The effluent is then freeze-dried to obtain a crude powder containing Fortimicin A in a free base form.

Silica gel chromatography, for example, is used as a method for isolating Fortimicin A from the crude powder. As a developer, the lower layer of a mixture of chloroform, isopropanol and aqueous ammonia (2:1:1) is used. More specifically, the crude powder is dissolved in the developing solvent, introduced into a column of silica gel and developed with the same solvent. The first active fraction contains Fortimicin B. Other trace components are eluted in successive fractions and then Fortimicin A is eluted out in fractions covering a wide range. The fractions containing Fortimicin A are collected and concentrated under reduced pressure. After freeze-drying the concentrate, a white powder comprising the base of the antibiotic is obtained. The thus obtained preparate of Fortimicin A has a comparatively high purity. However, the preparate is sometimes contaminated with impurities and, in such a case, the preparate is subjected to cellulose column chromatography with a solvent mixture of n-butanol, pyridine, acetic acid and water (6:4:2:4) as a developer. The active fractions obtained thereby are collected and concentrated under reduced pressure, whereby a pure preparate of Fortimicin A is obtained. When the impurity is a substance positive in the ninhydrin test, the removal thereof may be carried out by carboxymethylcellulose column chromatography. More specifically, a solution of the crude powder of Fortimicin A is passed through a column packed with carboxymethylcellulose (ammonium form). Active substances are adsorbed on the carboxymethylcellulose. After well washing the column with water to remove most pigments and inorganic salts therefrom, elution is carried out with 0.2N ammonium bicarbonate. The thus purified active fractions of Fortimicin A are collected and freeze-dried.

In the above purification procedures, the active fractions of Fortimicin A are determined by an ascending paper chromatography using Whatman No. 1 filter paper. Development is carried out at room temperature for 10 to 15 hours using the lower layer of a solvent mixture of chloroform, methanol and 17% aqueous ammonia (2:1:1). The Rf value of Fortimicin A on the paper chromatogram is about 0.37.

Fortimicin A is a white, basic powder. The elementary analytical values as found are C=50.2%, H=8.67%, N=17.5% and O=23.6%. The molecular weight is 405 (calculated based on the results obtained by high resolution mass spectrometry). Accordingly, the molecular formula is considered to be $C_{17}H_{35}N_5O_6$. The elementary analytical values as calculated are C=50.4%, H=8.64%, N=17.3% and O=23.7%. The melting point is higher than 200°C (decomposed).

FIG. 1 illustrates the ultraviolet absorption spectrum of an aqueous solution of Fortimicin A. The spectrum reveals no characteristic maximum absorption between 220 and 360 m$\mu$, and shows simply a terminal absorption.

The optical rotation of the free base of Fortimicin A is $[\alpha]_D^{25} = +26°$ (C=0.2, H$_2$O).

FIG. 2 illustrates the infrared absorption spectrum of Fortimicin A. As is apparent from the figure, Fortimicin A shows peaks at the following wavelengths (cm$^{-1}$):

3400, 2900, 1625, 1570, 1480,
1390, 1340, 1100, 1030.

The free base of Fortimicin A is very soluble in water, also soluble in methanol and slightly soluble in ethanol and acetone, but insoluble in such organic solvents as chloroform, benzene, ethyl acetate, butyl acetate, ethyl ether, butanol, petroleum ether, n-hexane, etc.

Fortimicin A gives positive reactions in the ninhydrine test and potassium permanganate test, and gives negative reactions in the Elson-Morgan's test and biuret test.

Based upon studies conducted upon the antibiotic, it is presently believed that Fortimicin A is of the following chemical structure:

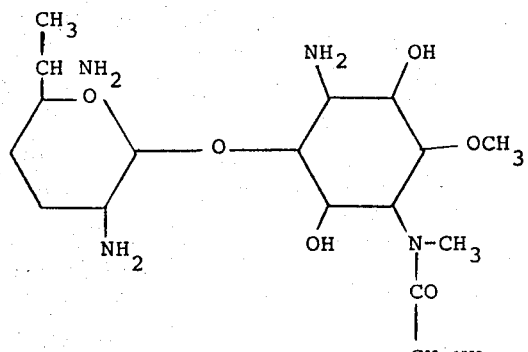

However, it is to be understood that the foregoing chemical structure is unconfirmed and the nature and identification of Fortimicin A should be made according to the above procedures.

The Rf values of Fortimicin A obtained as a result of paper chromatography and thin layer chromatography using various developers are shown in the following tables 3, 4 and 5. These values are compared with the Rf values of various similar antibiotics developed in the same manner.

Table 3

Rf values of Fortimicin A in ascending paper chromatography (at 28°C)

| Developer | Rf value | Developing period (hour) |
| --- | --- | --- |
| 20% Ammonium chloride | 0.96 | 3 |
| Water-saturated n-butanol | 0.00 | 15 |
| n-Butanol-acetic acid-water (3:1:1) | 0.06 | 15 |
| Water-saturated ethyl acetate | 0.00 | 4 |
| Water-saturated n-butanol containing 2% (W/V) p-toluene-sulfonic acid and | | |

Table 3-continued

Rf values of Fortimicin A in ascending paper chromatography (at 28°C)

| Developer | Rf value | Developing period (hour) |
| --- | --- | --- |
| 2% (V/V) piperidine | 0.04 | 15 |

Table 4

Rf values of Fortimicin A, Gentamicin C complex and Gentamicin C$_2$ in silica gel thin layer chromatography (developed at room temperature for 3 hours)

| Developer* | Antibiotic | Rf value |
| --- | --- | --- |
| I | Fortimicin A | 0.74 |
| I | Gentamicin C complex | 0.71 |
| I | Gentamicin C$_2$ | 0.71 |
| II | Fortimicin A | 0.37 |
| II | Gentamicin C complex | 0.06 – 0.16 |
| II | Gentamicin C$_2$ | 0.08 – 0.14 |

*Developer I:
The upper layer of the mixture of chloroform, methanol and 17% aqueous ammonia (2:1:1 by volume)
Developer II:
10% ammonium acetate and methanol (1:1 by volume)

Table 5

Rf values of known antibiotics in ascending paper chromatography using as a developer the lower layer of the mixture of chloroform, methanol and 17% aqueous ammonia (2:1:1) (developed at room temperature for 12 hours)

| Antibiotic | Rf value |
| --- | --- |
| Streptomycin A | 0.02 |
| Streptomycin B | 0.00 |
| Bluensomycin | 0.01 |
| Ribostamycin | 0.00 |
| Lividomycin A | 0.00 |
| Lividomycin B | 0.03 |
| Lividomycin D | 0.02 |
| Spectinomycin | 0.45 |
| Kasugamycin | 0.01 |
| Butirosin A | 0.00 |
| Butirosin B | 0.01 |
| Hygromycin B | 0.02 |
| Gentamicin A | 0.00 |
| Gentamicin B | 0.00 |
| Gentamicin C$_{1a}$ | 0.18 |
| Gentamicin C$_1$ | 0.59 |
| Gentamicin C$_2$ | 0.38 |
| Sisomicin | 0.18 |
| Neomycin A | 0.00 |
| Neomycin B | 0.03 |
| Antibiotic No. 460 | 0.01 |
| Neomycin C | 0.00 |
| Kanamycin A | 0.02 |
| Kanamycin B | 0.01 |
| Kanamycin C | 0.02 |
| Paromomycin | 0.00 |
| Nebramycin complex | 0.01 |
| Tobramycin | 0.02 |
| Apramycin | 0.02 |
| Nebramycin factor 4 | 0.01 |
| Nebramycin factor 5 | 0.00 |
| Myomycin | 0.00 |
| XK-62-2* | 0.49 |
| XK-70-A** (Fortimicin B) | 0.65 |
| XK-70-1 (Fortimicin A) | 0.37 |

*A new antibiotic disclosed in copending U.S. Pat. Application Ser. No. 364,058; filed May 25, 1973.
**A new antibiotic disclosed in U.S. Pat. Application Ser. No. 458,422; Filed April 5, 1974.

The antibacterial spectra of Fortimicin A against various microorganisms by agar dilution method (pH 8.0) are shown in the following Table 6.

TABLE 6

| Microorganism tested | Minimum inhibitory concentration (γ/ml) |
| --- | --- |
| Streptococcus faecalis ATCC 10541 | 10 |
| Bacillus subtilis No. 10707 | 0.02 |
| Bacillus cereus ATCC 9634 | 0.6 |
| Bacillus cereus var. mycoides ATCC 9463 | 0.6 |
| Staphylococcus aureus ATCC 6538P | 0.04 |
| Staphylococcus aureus KY 8942 (resistant to Kanamycin, Paramomycin, Streptomycin, Gentamicin and Nebramycin) | 10 |
| Staphylococcus aureus KY 8950 (resistant to Streptomycin, Tetracycline, Penicillin and sulfonamide) | 1.3 |
| Staphylococcus aureus KY 8953 (resistant to Streptomycin, Kanamycin, Paromomycin, Tetracycline, Neomycin, Kanamycin B and Erythromycin) | 1.3 |
| Staphylococcus aureus KY 8956 (resistant to Streptomycin, Paromomycin, Tetracycline, Erythromycin and Oleandomycin) | 0.32 |
| Staphylococcus aureus KY 8957 (resistant to Chloramphenicol, Streptomycin, Kanamycin B, Tetracycline and Paromomycin) | 0.32 |
| Klebsiella pneumoniae ATCC 10031 | 0.08 |
| Escherichia coli ATCC 26 | 0.16 |
| Escherichia coli KY 8302 (resistant to Chloramphenicol, Streptomycin, Kanamycin, Paromomycin, Tetracycline and Spectinomycin) | 0.26 |
| Escherichia coli KY 8310 (resistant to Chloramphenicol, Streptomycin, Kanamycin, Gentamicin, Kanamycin B, Paromomycin, Tetracycline and Spectinomycin) | 0.13 |
| Escherichia coli KY 8314 (resistant to Streptomycin) | 0.26 |
| Escherichia coli KY 8315 (resistant to Streptomycin, Kanamycin, Paromomycin and Neomycin) | 0.13 |
| Escherichia coli KY 8327 (resistant to Kanamycin, Gentamicin, Sisomicin and Tobramycin) | 0.13 |
| Escherichia coli KY 8331 (resistant to Kanamycin, Ribostamycin, Neomycin, Paromomycin and Lividomycin) | 0.3 |
| Escherichia coli KY 8332 (resistant to Kanamycin and Tobramycin) | 0.3 |
| Pseudomonas aeruginosa BMH No. 1 | 5 |
| Pseudomonas aeruginos KY 8510 (resistant to Kanamycin, Kanamycin B, Tobramycin, Gentamicin $C_{1a}$ and Ribostamycin) | 5 |
| Proteus vulgaris ATCC 6897 | 0.16 |
| Proteus vulgaris KY 4296 (resistant to nalidixic acid) | 0.41 |
| Proteus vulgaris Abbott JJ, KY 4295 | 0.8 |
| Proteus mirabilis Finland 9 KY 4293 | 0.8 |
| Proteus mirabilis No. 825 KY 4292 | 0.41 |
| Proteus mirabilis No. 39 KY 4290 | 0.8 |
| Proteus morganii Jenkins KY 4298 | 1.6 |
| Proteus rettgeri Booth KY 4288 | 0.8 |
| Proteus rettgeri Hambrook KY 4289 | 0.41 |
| Shigella sonnei ATCC 9290 | 0.3 |
| Salmonella typhosa ATCC 9992 | 0.08 |

It is evident from the above that Fortimicin A has a wide range of activity against Gram-positive and Gram-negative bacteria, and also has a strong antibacterial activity against Staphylococcus aureus and Escherichia coli which are resistant to various known antibiotics. Particularly, Fortimicin A is characterized by showing a strong antibacterial activity against microorganisms of Escherichia coli and Staphylococcus aureus normally resistant to Kanamycin, Gentamicin, Tobramycin and the like, and also a satisfactory antibacterial activity against bacteria of the genus Proteus. It has been found that when used in the therapy of various infectious diseases caused by the above-mentioned bacteria, Fortimicin A exhibits remarkable therapeutic effects. In this respect, in vivo tests have been conducted on mice infected intraperitoneally with Escherichia coli Juhl KY 4286. The thus infected mice were treated with various concentrations of Fortimicin A by subcutaneous infection. As a result the $ED_{50}$ of Fortimicin A has been determined to be 6mg/kg. In view of the excellent antibacterial activity, the present substance, Fortimicin A, is considered to be useful in medical treatment as an antibacterial substance. Moreover, in view of the foregoing wide antibacterial spectrum, Fortimicin A may also be useful as a surface antibacterial agent.

A comparison of Fortimicin A with other antibiotics further illustrates its novelty. As water-soluble, basic antibiotics produced by microorganisms of the genus Micromonospora, having a wide antibacterial spectrum, there are such antibiotics as Gentamicin [M. J. Weinstein et al.: Antimicrobial Agents and Chemotherapy 1963, page 1; D. J. Cooper et al.: J. Infect. Dis., 119, 342 (1969); and J. A. Waitz: Antimicrobial Agents and Chemotherapy 2, 464 (1972)], Antibiotic No. 460 (Japanese Pat. No. 16153/71), Sisomicin [M. J. Weinstein et al.: J. Antibiotics, 23, 551, 555, 559 (1970)], XK-62-2 (U.S. patent application Ser. No. 364,058; filed May 25, 1973), Fortimicin B (U.S. patent application Ser. No. 458,422, filed Apr. 5, 1974) etc. However, as is evident from Table 5, the Rf values of Gentamicin A, B, $C_{1a}$ and $C_1$ are 0.00, 0.00, 0.18 and 0.59 and that of Fortimicin A is 0.37. Therefore, Fortimicin A is different from these Gentamicins. On the other hand, the Rf value of Gentamicin $C_2$ is 0.38 and that of Fortimicin A is 0.37. These values are very close. However, the Rf values of Gentamicin $C_2$ and Fortimicin A measured in silica gel thin layer chromatography using the developer II are respectively 0.08–0.14 and 0.37. Accordingly, Fortimicin A is different from Gentamicin $C_2$. Further, when compared with Antibiotic No. 460, Sisomicin, SK-62-2 and Fortimicin B, it is apparent that Fortimicin A is different from these antibiotics since the Rf values of Antibiotic No. 460, Sisomicin, XK-62-2 and Fortimicin B shown in Table 3 are respectively 0.01, 0.18, 0.49 and 0.65, whereas the corresponding Rf value of Fortimicin A is 0.37.

As water-soluble, basic antibiotics produced by microorganisms of Actinomycetes other than those of the genus Micromonospora, which have a wide antibacterial spectrum, there are such antibiotics as Streptomycin, Ribostamycin, Lividomycin, Spectinomycin, Kasugamycin, Neomycin, Kanamycin, Nebramycin, Promomycin, etc. Fortimicin A is greatly different from these antibiotics in physical and chemical properties. From the Rf values in paper chromatography shown in Table 3 it is evident that Fortimicin A is different from these known antibiotics.

Since Fortimicin A contains basic groups, it can exist in the form of acid addition salts. Accordingly, the present invention contemplates the pharmaceutically non-toxic acid addition salts of the antibiotic including the mineral acid addition salts such as hydrochloride, hydrobromide, hydroiodide, sulfate, sulfamate and phosphate and the organic addition salts such as the maleate, acetate, citrate, oxalate, succinate, benzoate, tartrate, fumarate, malate, mandelate, ascorbate and the like.

Practice of certain specific embodiments of the invention is illustrated by the following representative examples.

EXAMPLE 1

In this example, *Micromonospora olivoasterospora* MK-70 (ATCC 21819) (FERM-P No. 1560) is used as a seed strain. One loopful of the seed strain is inoculated into 10 ml of a seed medium containing 2% glucose, 0.5% peptone, 0.5% yeast extract and 0.1% calcium carbonate (pH 7.5 before sterilization) in a 50 ml large test tube. Culturing is carried out at 30°C for 5 days. Ten ml of the seed culture broth is then inoculated into 30 ml of a second seed medium in a 250 ml Erlenmeyer flask. The composition of the second seed medium is the same as that of the first seed medium. The second seed culturing is carried out at 30°C for 2 days with shaking.

Then 30 ml of the second seed culture broth is inoculated into 300 ml of a third seed medium in a 2 L Erlenmeyer flask provided with baffles. The composition of the third seed medium is the same as that of the first seed medium. The third seed culturing is carried out at 30°C for 2 days with shaking and 1.5 L of the third seed culture broth (corresponding to the content of five flasks) is inoculated into 15 L of a fourth seed medium in a 30 L glass jar fermenter. The composition of the fourth seed medium is the same as that of the first seed medium. Culturing in the jar fermenter is carried out at 37°C for 2 days with aeration and stirring (revolution: 350 r.p.m.; aeration: 15 L/min). Thereafter, 15 L of the fourth seed culture broth is inoculated into 150 L of a main fermentation medium in a 300 L fermenter. The main fermentation medium comprises 4% soluble starch, 2% soybean meal, 1% corn steep liquor, 0.05% $K_2HPO_4$, 0.05% $MgSO_4 \cdot 7H_2O$, 0.03% KCl and 0.1% $CaCO_3$ (pH 7.5 before sterilization). Culturing in the fermenter is carried out at 37°C for 4 days with aeration and stirring (revolution: 150 r.p.m.; aeration: 80 L/min).

After the completion of culturing, the resulting fermentation broth is adjusted to a pH of 2.5 with concentrated sulfuric acid, and stirred for 30 minutes. Then, about 7 kg of a filter aid, Radiolite No. 600 (product of Showa Kagaku Kogyo Co., Ltd., Japan) is added thereto and the microbial cells are removed by filtration. The filtrate is adjusted to a pH of 7.5 with 6N sodium hydroxide and passed through a column packed with about 20 L of a cation exchange resin, Amberlite IRC-50 (ammonium form), and the effluent is discarded. Active substances are adsorbed on the resin. After washing the resin with water, the adsorbed active substances are eluted out with 1N aqueous ammonia. Activity of the eluate is determined by a paper disc method, using an agar plate of *Bacillus subtilis* No. 10707. The active fractions are collected and the mixture is concentrated to about 1 L under reduced pressure. The concentrate is passed through a column packed with 500 ml of an anion exchange resin, Dowex 1 × 2 ($OH^-$ form). Then, about 2 L of water is passed through the column, whereby impurities are removed and active substances are eluted out. The thus obtained active fractions are collected, and concentrated to about 100 ml under reduced pressure, and the resulting concentrate is passed through a column packed with about 50 ml of active carbon powder. The active substances are adsorbed onto the carbon powders. Then, the column is washed with water and the effluent and the washing water are discarded. Then, the adsorbed active substances are eluted out with 0.2N sulfuric acid. Activity of the eluate is determined by the paper disc method using *Bacillus subtilis*, and the active fractions are collected. The thus obtained fractions are passed through a column of Dowex 44 ($OH^-$ form), and active substances are eluted out with water. The active fractions are again collected and concentrated to about 50 ml. The thus obtained concentrate is lyophilized, whereby about 32 g of a crude powder containing Fortimicin A is obtained. The crude powder exhibits an activity of 575 unit/mg (the activity of 1 mg of a pure product corresponds to 1000 units).

Then 10 g of the crude powder is placed as a thin and uniform layer on 500 ml of silica gel packed in a glass column. The glass column is prepared by suspending the silica gel in a solvent of the lower layer of a mixture comprising chloroform, isopropanol and 17% aqueous ammonia (2:1:1 by volume), and then packing the suspension tightly in the column as a uniform layer, and thereafter washing with the same solvent. After placing the crude powder at the head of the column, elution is carried out with the above-described solvent by gradually pouring into the column from its top, and thereafter elution is carried out at a flow rate of about 50 ml/hour. The eluate is obtained as fractions of 20 ml each, and the activity of each fraction is determined by a paper disc method. Fortimicin B is eluted out at first. Thereafter, fractions containing Fortimicin A are obtained. The active fractions are subjected to paper chromatography, and the fractions containing Fortimicin A are collected and concentrated under reduced pressure to completely remove the solvent. The concentrate is then dissolved in a small amount of water. After freeze-drying the solution, about 1.8 g purified preparate of the free base of Fortimicin A is obtained. The activity of the preparate is about 970 unit/mg.

EXAMPLE 2

In this example the same seed strain and first through fourth seed culturing of Example 1 is repeated. As the main fermentation medium, a medium having the following composition is used:

| | |
|---|---|
| Soluble starch | 4% |
| Ebios (dried yeast powder, produced by Tanabe Pharmaceutical Co., Japan) | 3% |
| $K_2HPO_4$ | 0.05% |
| $MgSO_4 \cdot 7H_2O$ | 0.05% |
| KCl | 0.03% |
| $CaCO_3$ | 0.1% |

Culturing is carried out in the same manner as in Example 1. Isolation of a crude powder containing Fortimicin A is carried out in the same manner as in Example 1, whereby about 63 g of a crude powder having an activity of about 650 unit/mg is obtained. According to the method of Example 1, the crude powder is purified, whereby about 18 g of purified Fortimicin A having an activity of about 850 unit/mg is obtained. The thus obtained preparate is further purified by cellulose column chromatography. Specifically, the preparate is placed as a thin and uniform layer on about 500 ml of cellulose powder (AVICEL, Funakoshi Yakuhin Co., Ltd.) packed in a glass column. The column is prepared by suspending cellulose powder in a solvent mixture of n-butanol, acetic acid, pyridine and water (6:2:4:4). The suspension is then tightly packed in the glass column as a uniform layer, and then well washed with the same solvent. After the placing of the preparate at the head of the column, elution is carried out with the same solvent by gradually pouring the column into the column from its top, and then continuing elution at a flow rate of about 1 ml/minute. The eluate is obtained as fractions of 10 ml each, and the activity of each fraction is determined by a paper disc method. The active fractions are collected and concentrated under reduced pressure to completely remove the solvent. The concentrate is dissolved in a small amount of water. After freeze-drying the solution, about 9 g of a purified preparate of the base of Fortimicin A is obtained. The activity of this preparate is 980 unit/mg.

EXAMPLE 3

In this example, the same seed strain and the first through fourth seed culturing of Example 1 is repeated. As the main fermentation medium, a medium having the following composition is used:

| | |
|---|---|
| Soluble starch | 4% |
| Casamino acid (an acid hydrolyzate of casein, produced by DIFCO Labs. U.S.A.) | 3% |
| $K_2HPO_4$ | 0.05% |
| $MgSO_4 \cdot 7H_2O$ | 0.05% |
| KCl | 0.03% |
| $CaCO_3$ | 0.1% |

Culturing, isolation and purification of Fortimicin A are carried out in the same manner as in Example 1, whereby about 18.5 g of a purified preparate of Fortimicin A having an activity of about 965 unit/mg is obtained.

EXAMPLE 4

In this example, a culture broth obtained by carrying out fermentation in the same manner as in Example 1 is subjected to a paper chromatography to confirm the presence, in substantial amounts, of Fortimicin A. The broth is then treated in the same manner of Example 1 to obtain a crude powder containing Fortimicin A. Then, 3 g of the resulting crude powder is dissolved in 5 ml of water and the solution is poured into a column packed with about 200 ml of carboxymethylcellulose (ammonium form). Thereafter, about 1000 ml of water is passed through the column whereby active substances are adsorbed on the carboxymethylcellulose and most of the not-adsorbed pigments and inorganic salts are removed. Elution is then carried out with 0.2M citric acid-phosphoric acid buffer solution (pH: 3.0) at a flow rate of about 50 ml/hour and the eluate is collected as fractions of 10 ml each. The activity of each fraction is determined by a paper disc method. The active fractions are subjected to paper chromatography, and the fractions containing Fortimicin A are collected. The Fortimicin A fractions are passed through a column of Amberlite CG-50 (H $^+$ form) whereby the active substances are adsorbed on the resin. After washing the column with water, elution is carried out with 0.5N hydrochloric acid. The active fractions are collected and then passed through a column of Dowex 44 (OH$^-$ form) for neutralization. The resulting effluent is freeze-dried, whereby about 560 mg of the free base of Fortimicin A is obtained. The activity of the product is about 985 unit/mg.

EXAMPLE 5

In this example, *Micromonospora olivoasterospora* Mm 744, KY 11067 (FERM-P No. 2193, ATCC 31009) is used as the seed strain. The first through fourth seed culturing is carried out in the same manner as Example 1 using a seed medium containing 2% glucose, 0.5% peptone, 0.3% yeast extract, 0.1% calcium carbonate (pH: 7.2 before sterilization). Then 15 L of the fourth seed culture broth is inoculated into 150 L of a main fermentation medium in a 300 L stainless steel fermenter. The main fermentation medium comprises 2% soluble starch, 0.5% soybean meal, 2% glucose, 1% corn steep liquor, 1% yeast extract, 0.05% $K_2HPO_4$, 0.05% $MgSO_4 \cdot 7H_2O$, 0.03% KCl and 0.1% $CaCO_3$ (pH: 7.0 before sterilization). Culturing is carried out at 30°C for 4 days with aeration and agitation (revolution: 150 r.p.m., aeration: 80 L/min). After the completion of culturing about 42 g of a crude powder containing Fortimicin A is obtained from the fermentation broth in the same manner as in Example 1. The activity of the crude powder is about 560 unit/mg. The thus obtained crude powder is then subjected to purification as in Example 1, whereby about 6.8 g of the free base of Fortimicin A is obtained. The activity of the product is about 975 unit/mg.

EXAMPLE 6

In this example *Micromonospora olivoasterospora* MK 80, KY 11055 (FERM-P No. 2192, ATCC 31010) is used as the seed strain. The seed strain is seed cultured in four steps as in Example 1 using a seed medium comprising: 1% glucose, 1% soluble starch, 0.5% yeast extract, 0.5% peptone and 0.1% calcium carbonate (pH: 7.0 before sterilization). The seed culture broth from the fourth seed culturing is then inoculated in a main fermentation medium as in Example 1. However, in this example the fermentation medium of Example 5 is used. From the resulting main fermentation broth, about 52 g of a crude powder containing Fortimicin A is obtained following the same procedure of Example 1. The activity of the crude powder is about 530 unit/mg. The thus obtained crude powder is then subjected to purification according to the same manner of Example 1, whereby about 9 g of the free base of Fortimicin A is obtained. The activity of the product is about 980 unit/mg.

What is claimed is:
1. The antibiotic Fortimicin A characterized by:
    (a) a molecular weight of 405;
    (b) the molecular formula of $C_{17}H_{35}N_5O_6$;
    (c) an ultraviolet absorption spectrum essentially as shown in FIG. 1; and
    (d) an infrared absorption spectrum essentially as shown in FIG. 2 or its pharmaceutically acceptable acid salts.

* * * * *